United States Patent [19]
Lamberti et al.

[11] 3,986,986
[45] Oct. 19, 1976

[54] NOVEL 2-(ALKYLSULFINYL)ETHYL SULFATES AND COMPOSITIONS EMPLOYING SAME

[75] Inventors: Vincent Lamberti, Upper Saddle River; Wilder F. Pease, Norwood, both of N.J.

[73] Assignee: Lever Brothers Company, New York, N.Y.

[22] Filed: July 21, 1975

[21] Appl. No.: 597,722

Related U.S. Application Data

[62] Division of Ser. No. 476,809, June 6, 1974, Pat. No. 3,940,433.

[52] U.S. Cl. .............................. 252/526; 252/527; 252/531; 252/545; 252/550
[51] Int. Cl.² .................... C11D 1/12; C11D 3/065
[58] Field of Search .......................... 252/531, 550; 260/458 R

[56] References Cited

UNITED STATES PATENTS

| | | | |
|---|---|---|---|
| 2,909,554 | 10/1959 | Doerr | 260/458 R |
| 3,480,556 | 11/1969 | De Witt | 260/458 R |
| 3,714,076 | 1/1973 | Anderson | 252/550 |

FOREIGN PATENTS OR APPLICATIONS

| | | |
|---|---|---|
| 435,039 | 9/1935 | United Kingdom |

*Primary Examiner*—P.E. Willis, Jr.
*Attorney, Agent, or Firm*—Kenneth F. Dusyn; James J. Farrell; Melvin H. Kurtz

[57] ABSTRACT

The instant invention relates to a class of novel compounds having utility as surfactants in detergent compositions and also to detergent and other compositions employing said novel compounds.

19 Claims, No Drawings

NOVEL 2-(ALKYLSULFINYL)ETHYL SULFATES AND COMPOSITIONS EMPLOYING SAME

This is a division, of application Ser. No. 476,809, filed June 6, 1974 now U.S. Pat. No. 3,940,433.

BACKGROUND OF THE INVENTION

This invention relates to the field of sufactants and their use in detergent compositions, including laundry and dishwashing compositions, in dentifrice and mouthwash compositions and in shampoo and toilet bar compositions. The applicants have discovered a novel class of compounds, i.e. 2-(alkylsulfinyl)ethyl sulfates, which are useful as biodegradable surfactants.

It is well known that in recent years there have been studies concerning the eutrophication of waters and the biodegradability, or lack thereof, of substances that find their way into said waters and contribute to said eutrophication. For environmental reasons it is imperative that detergent compositions contain components that are biodegradable.

The 2-(alkylsulfinyl)ethyl sulfates of the instant invention have been found to possess the necessary detergency and biodegradability requirements for use as detergent active components in both non-phosphate and phosphate dishwashing, light and heavy duty detergent compositions.

Light-duty applications are those such as the hand washing of dishware and lightly soiled fine fabrics which fabrics cannot as a rule withstand the vigorous treatment of machine laundering. Also, light-duty washing situations are those which generally call for a gentle washing action in cool or lukewarm water. It is well known by those skilled in the art that compositions designed for such uses must have certain performance properties which distinguish them from heavy-duty cleaning compositions. For instance, they must be mild to the skin, possess high sudsing properties, and also possess cleaning power in water solutions having cool or lukewarm temperatures, e.g., below 100° F.

The term "heavy-duty" applications are those cleaning situations in which heavily soiled articles are encountered. Considerations in such cleaning processes include the use of vigorous mechanical action usually in hot water having temperatures below about 120° F up to about 200° F. Moreover, the problems presented by high soil loads or fabrics such as cotton are unlike those dealt with in light-duty situations. As a result, heavy-duty detergent compositions must be specially formulated.

In the formulation of "heavy-duty" built detergent laundering compositions, the most valuable detergents are those which combine effective cleaning ability with superior whiteness maintenance results. Cleaning pertains to the removal of soil from soiled articles. Whiteness maintenance is a term which is used to measure the ability of an aqueous solution of a detergent composition to keep suspended in the solution, soil which has been removed during the washing process.

There has long been a need for a built detergent composition which can be used with superior effectiveness in both light-duty and heavy-duty cleaning situations. This implies, of course, satisfactory performance in washing solutions where temperature ranges anywhere from about 50° F up to about 200° F and higher. Literally thousands of active detergent compounds have been tried, alone and in combination with other detergents and builders, as well as other detergent aids such as sequestering agents in order to satisfy this need of longstanding. For the most part, such attempts have not been satisfactory.

Of particular importance is the need for a detergent composition that efficiently cleans without the need of the commonly used phosphorus-containing builder salts. Sequestrant builder salts such as sodium tripolyphosphate (STP) are normally included in built detergent compositions partly for the purpose of sequestering hardness ions, especially calcium, that are found in water. In the absence of these sequestrant builders a water-insoluble hardness ion salt will be deposited on the laundered fabrics and as a result, will adversely affect the overall cleaning performance of the detergent. Recent fears of the effect of STP and other phosphorus-containing sequestrant builders on the ecology have caused a great amount of research in the area of finding a suitable replacement. Most replacements to date have not been as good as STP with regard to preventing the formation of the water-insoluble salt of the detergent. This absence of a fully satisfactory replacement for STP has, accordingly, led some to look for a detergent that is better able to perform properly with other known builders. Preferably the novel detergent would be relatively calcium insensitive, i.e. would not form a water-insoluble salt with the calcium found in the water. In this way the detergent could be used in a heavy-duty application without the need of a builder or with builders considered to have weak sequestering properties. Unfortunately, the complex nature of how a detergent works has made the search for an effective detergent very difficult.

DESCRIPTION OF THE PRIOR ART

The need and search for improved detergent compositions is a continuing one. Countless new surface active materials have been and are being prepared, of which only a relative few may eventually be found suitable for commercial use as detergent materials in toilet bars, dishwashing compositions, light and heavy duty built laundry compositions.

Alkyl sulfoxides having a long chain fatty acid residue are known to have surface active properties. U.S. Pat. No. 2,787,595 to Webb discloses the use of alkyl sulfoxides as the essential active ingredient in detergent compositions. According to Webb, the sulfoxides may be employed either alone or in combination with builders. A patent to Louthan, U.S. Pat. No. 2,864,866 teaches the preparation of sulfoxides by the oxidation of glycol thioethers using, inter alia, hydrogen peroxide as the oxidizing agents. A series of U.S. Patents to Priestly viz., U.S. Pat. Nos. 3,382,180; 3,660,497; 3,670,027; and 3,739,031, relate to preparation and use of hydroxysulfoxides in detergent compositions. U.S. Pat. No. 3,382,180 relates specifically to the use of alkyl monosulfoxides as suds stabilizers in detergent compositions. A patent, U.S. Pat. Nos. 2,017,004, to Keistahler et al, describes the oxidation and sulfation of organic sulfides to form sulfones, said patent incorporated herein by reference. The compounds disclosed herein and their use in detergent compositions have not been described heretofore in the literature.

DESCRIPTION OF THE INVENTION

In accordance with the instant invention novel compounds are provided having the structure

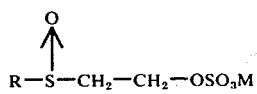

wherein R is a straight or branched chain saturated aliphatic radical having from about 10–20 carbon atoms and M is hydrogen, an alkali metal, ammonium, alkyl substituted ammonium and alkylolammonium cation, said alkyl groups having from 1–6 carbon atoms.

The alkali metal salts may be selected from sodium, potassium and lithium. The alkyl moiety of the substituted ammonium cation and the alkylol ammonium cation is a straight or branched chain saturated aliphatic radical having from one to six carbon atoms. Illustrative examples are methyl, ethyl, propyl, isopropyl, butyl, isobutyl, tertiary butyl, pentyl, isopentyl, hexyl, isohexyl, hydroxyethyl and hydroxypropyl.

The members of this class of compounds are readily prepared by reacting an olefin, e.g. 1-tetradecene, with 2-mercaptoethanol using a free radical initiator, e.g. azobisisobutyronitrile (AIBN), as catalyst to obtain an intermediate alkylhydroxyethyl sulfide. The intermediate is subsequently oxidized with hydrogen peroxide under reflux in the presence of acetone to the 2-(alkylsulfinyl)ethanol. This compound is subsequently slurried with methylene chloride. A separate solution of liquid sulfur trioxide and methylene chloride is made. The two solutions are mixed with stirring. After a period of time the reaction mixture is treated with sodium hydroxide, thus yielding the sodium salt of 2-(alkylsulfinyl)ethyl sulfate. The reactions involved may be expressed by the following equations:

  (1)

  (2)

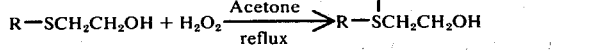  (3)

  (4)

R' and R'' may be hydrogen or an alkyl group with the proviso that the total number of carbon atoms in R' and R'' is from 8–18 and with the further proviso that both R' and R'' cannot simultaneously be hydrogen. R thus is a saturated straight or branched aliphatic group having from 10–20 carbon atoms.

This process is applicable to all the members within the homologous series embracing the instant class of novel compounds, including odd chain length members. Within the class of olefins contemplated herein as starting materials are also dimer olefins and internal olefins.

As aforestated, the novel 2-(alkylsulfinyl)ethyl sulfates of the instant invention are useful as detergent actives in light or heavy duty laundry compositions and also in mechanical dishwasher compositions. These compounds may also be used in dentifrices and shampoos.

Accordingly, it is also an objective of the instant invention to formulate detergent compositions utilizing the novel 2-(alkylsulfinyl)ethyl sulfates, which detergent compositions are outstandingly suitable for light duty and heavy duty applications, etc., as described above, and further which perform well at washing solution temperatures ranging from about 50° F to about 200° F.

One of the features of the instant class of compounds is that the higher members provide good detergency with low foaming properties. This feature is particularly important since it enables utilization of the more readily available higher α-olefins, e.g. $C_{16}$ to $C_{20}$ from which the compounds of the invention are derived. Furthermore, the low foaming properties are especially important since the compounds may be used as replacements for nonionic surfactants particularly those based on ethylene oxide. Replacement of nonionic surfactants has become an important objective in the detergent art because of recurring shortages of ethylene oxide from which the nonionics are generally made. It is noteworthy that the 2-mercaptoethanol used to make the instant compounds is derived from only one mole of ethylene oxide per mole of compound in contrast to well-known nonionic surfactants which utilize from 7 to about 13 moles of ethylene oxide per mole of compond. The instant compounds, which are anionic in nature, therefore, are highly desirable surfactants from a raw materials point-of-view in the detergent field.

The higher members, especially the $C_{16}$ and $C_{18}$ alkyl homologues, also have excellent lime-soap dispersing properties and, accordingly, find utility in soap formulations (e.g. bars and powders) and in detergent bar formulations. In addition, the $C_{16}$ to $C_{20}$ alkyl homologs have useful softening properties and thus find use in softening compositions.

Another important feature of the series of compounds of the instant invention is that the middle members, i.e. the $C_{12}$ to $C_{16}$ alkyls are relatively insensitive to hardness ions in contrast to the corresponding alkyl sulfates which precipitate hardness ions. These compounds, especially the $C_{14}$ alkyl homolog which has excellent foaming properties, are admirably suited for use in hand dishwashing formulations, dentifrice/mouthwash compositions, shampoos, bubble bath compositions, soap and detergent bars and the like.

Finally, where wetting action is desired with a minimum of foam or a quick-breaking foam (e.g. hard surface cleansers) the $C_{10}$ alkyl compound has the desired properties.

It is our belief, although not wishing to be bound by such, that the presence of the sulfoxide moiety greatly reduces the calcium sensitivity of the compound, as compared to the corresponding alkyl sulfates. Further, it is also our belief that the presence of the sulfoxide moiety results in compounds which are less irritating to the skin. These factors render the novel compounds of this invention as a reliable and attractive alternative to conventional sulfate detergent actives viz., sodium alkyl sulfates, which are known to be calcium sensitive and the lower members of which are highly irritaing to the skin.

It has surprisingly been found that the novel 2-(alkylsulfinyl)ethyl sulfates may be employed per se as detergents in aqueous media; however their effectiveness is enhanced by combining them with up to about 50%, i.e. 0 - about 50%, water soluble inorganic or organic alkaline detergency builders to provide built detergent compounds. The weight ratio of detergent active to the builder is from about 10:1 to about 1:10. More precisely, the so-called light duty detergent compositions, i.e., those used for fine fabric and hand dishwashing, the active level is about 10 to about 40%, preferably, about 15% to about 25%. In the case of heavy duty detergent compositions, the active level is from about 5% to about 75%. In a mechanical dishwashing composition, however, the active is present in an amount of from about 0.5% to about 10%, preferably about 1% to about 5%. These compositions also contain from about 25% to about 75%, preferably 35% to 60% of an alkaline sequestrant builder (listed hereinafter) and generally sodium silicate as a corrosion inhibitor and alkalinity source, said silicate being present from about 5% to about 50%, preferably 10% to 25%. There is also present a chlorine bleach component from about 0.5% to about 25%, preferably 1% to 15%. Examples of the chlorine bleach components are dichlorocyanurates; 1,3-dichloro-5,5-dimethylhydantoin and others disclosed in U.S. Pat. No. 3,544,473, incorporated herein by reference.

Examples of suitable water-soluble inorganic alkaline detergency builder salts are alkali metal carbonates, borates, phosphates, polyphosphates, bicarbonates and silicates. Specific examples of such salts are sodium and potassium tetraborates, perborates, bicarbonates, carbonates, tripolyphosphates, pyrophosphates, orthophosphates, hexametaphosphates and silicates.

Examples of suitable organic alkaline detergency builder salts are: (1) water-soluble aminopolycarboxylates, e.g. sodium and potassium ethylenediaminetetraacetates, nitrilotriacetates and N-(2-hydroxyethyl)-nitrilodiacetates; (2) water-soluble salts of phytic acid, e.g. sodium and potassium phytates — see U.S. Pat. No. 2,739,942, incorporated herein by reference; (3) water-soluble polyphosphates, including specifically, sodium, potassium and lithium salts of ethane-1-hydroxy-1,1-diphosphonic acid, sodium, potassium and lithium salts of methylene diphosphonic acid, sodium, potassium and lithium salts of ethylene diphosphonic acid, and sodium, potassium and lithium salts of ethane-1,1,2-triphosphonic acid. Other examples include the alkali metal salts of ethane-2-carboxy-1,1-diphosphonic acid, hydroxymethane-diphosphonic acid, carbonyldiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid and propane-1,2,2,3-tetraphosphonic acid; (4) water-soluble salts of polycarboxylate polymers and copolymers as described in U.S. Pat. No. 3,308,067, incorporated herein by reference. Specifically, a detergent builder material comprising a water-soluble salt of a polymeric aliphatic polycarboxylic acid having the following structural relationships as to the position of the carboxylate groups and possessing the following prescribed physical characteristics: (a) a minimum molecular weight of about 350 calculated as to the acid form; (b) an equivalent weight of about 50 to about 80 calculated as to acid form; (c) at least 45 mole percent of the monomeric species having at least two carboxyl radicals separated from each other by not more than two carbon atoms; (d) the site of attachment of the polymer chain of any carboxyl-containing radical being by not more than three carbon atoms along the polymer chain from the site of attachment of the next carboxyl-containing radical. Specific examples are polymers of itaconic acid, aconitic acid, maleic acid, mesaconic acid, fumaric acid, methylene malonic acid and citraconic acid and copolymers with themselves and other compatible monomers such as ethylene; and (5) mixtures thereof.

Mixtures of organic and/or inorganic builders can be used and are generally desirable. One such mixture of builders is disclosed in U.S. Pat. No. 3,392,121, incorporated herein by reference, issued to Burton H. Gedge III wherein ternary mixtures of sodium tripolyphosphate, sodium nitrilotriacetate and trisodium ethane-1-hydroxy-1,1-diphosphonate are disclosed. The above described builders can also be utilized singly in this invention.

In addition, other builders can be used satisfactorily such as water-soluble salts of citric acid, mellitic acid, i.e. benzene hexacarboxylic acid, pyromellitic acid, benzene pentacarboxylic acid, oxydiacetic acid and oxydisuccinic acid and carboxymethyloxysuccinic acid (CMOS).

The detergent compositions of the present invention are especially useful in admixture with other materials to form complete formulations. Such complete formulations are prepared commercially in several forms including granular, flake, liquid and tablet forms.

It will also be understood that the compositions of this invention may include adjuvants, diluents and additives inclusive of from about 0% to about 25% detergent adjuvants, preferably from about 5% to about 20%, wherein said detergent adjuvants are soil suspending agents, hydrotropes, corrosion inhibitors, dyes, perfumes, fillers, buffers, optical brighteners, perborates, bleaches, bleach activators, enzymes, suds boosters, suds depressants, germicides, fungicides, antitarnishing agents, fabric softening agents, opacifiers or organic solvents. Commonly used fillers are sodium sulfate, sodium chloride and sodium silicate.

The novel surfactants can also be used in combination with conventional anionic, cationic, zwitterionic and amphoteric surfactants. Specific examples of the aforementioned classes of organic detergents are disclosed in U.S. Pat. No. 3,790,482 to Jones, et al. incorporated herein by reference. Netherlands Pat. No. 7,117,151 published July 10, 1972 discloses several examples of calcium insensitive surfactants, said publication incorporated herein by reference. These surfactants, in addition to the alkylsulfinyl surfactants, may be present in a detergent composition at a level of about 1% to about 60% based on the total weight of the composition. A typical composition employing these mixed surfactants may be as follows:

(a) 1% to about 75% of a surfactant having the structure

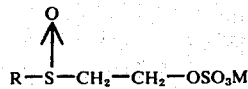

wherein R is a straight chain saturated aliphatic radical having from 10–20 carbon atoms and M is an alkali metal or ammonium cation, (b) 1% to about 60% of a detergent compound selected from the group consisting of anionic, nonionic, zwitterionic or ampholytic detergent compounds and mixtures thereof, (c) 0 to about 50% of a builder compound selected from the group consistng of water-soluble inorganic alkaline salts which include alkali metal carbonates, borates, phosphates, polyphosphates, bicarbonates and silicates and hexametaphosphates, and water-soluble organic alkaline salts which inclue aminopolycarboxylates, phytates, polyphosphonates, polycarboxylate homo and copolymers, citrates, mellitates, carboxymethyloxysuccinates and mixtures thereof, (d) from about 0% to about 25% detergent adjuvants wherein said detergent adjuvants are soil suspending agents, hydrotropes, corrosion inhibitors, dyes, perfumes, fillers, buffers, optical brighteners, perborates, bleaches, bleach activators, enzymes, suds boosters, suds depressants, germicides, fungicides, anti-tarnishing agents, fabric softening agents, opacifiers or organic solvents, and (e) the balance being water.

When the claimed surfactants are utilized in a dentifrice or mouthwash composition they are present at a level of from about 0.5% to about 5%, preferably 1% to about 3%. When used in shampoo compositions, the alkylsulfinylethyl sulfates are present from about 1% to about 20%, preferably from about 5% to about 15%.

The following, non-limiting examples are presented as illustrative of the instant invention.

EXAMPLE 1

The following example illustrates the preparation of the novel class of compounds of the instant invention.

(a) 1-Tetradecene, 100 g, (0.509 moles), 2-mercaptoethanol, 41.8 g, (.536 moles) and 0.1 g, azobisisobutyronitrile (AIBN) are placed in a 3 neck, 250 ml, round bottom flask. A magnetic stirring bar is added and the mixture stirred at 90°–95° on a water bath. Initially the mixture contains two phases but after heating and stirring for 10 minutes a clear solution results. This is heated to 95° for 1 hour longer. The crude n-tetradecylhydroxyethyl sulfide, was vacuum distilled and the fraction boiling at 168°–179° C (0.9 mm) collected.

The $C_{10}$ to $C_{16}$ alkyl homologs are made using this procedure. The higher alkyl homologs, $C_{17}$ to $C_{20}$ are made by reacting the appropriate α-olefin with 2-mercaptoethanol in the presence of 20–100 ml of isopropanol solvent per each 0.1 mole of olefin used in the presence of 0.2 g AIBN and refluxing the mixture for 5–8 hours. In the case of the $C_{17}$ homolog the product is taken up in ether and washed three times with 0.75N NaOH to remove unreacted mercaptoethanol and then, with water until neutral. The solvent is removed in vacuo and the residue dried at 60° C under water pump vacuum. The n-alkylhydroxyethyl sulfide product is then used directly in the oxidation reaction to produce the n-alkylsulfinylethanol as described below.

In the cases of the $C_{18}$ to $C_{20}$ alkyl homologs, the product, which crystallizes out of the reaction mixture, is simply filtered from the isopropanol reaction solvent. Additional product is obtained from the mother liquors by concentration and dilution with acetone. Recrystallization of the higher alkyl homologs is readily carried out with isopropanol.

The boiling points or melting points of the n-alkylhydroxyethyl sulfides appear below:

Table I

| Alkyl Group | Moles Reactants n-Alkene | $HSCH_2CH_2OH$ | Product B.P. or M.P. |
|---|---|---|---|
| $C_{10}$ | .700 | .700 | 121–127° C/0.6 mm |
| $C_{12}$ | .594 | .624 | 140–147° C/0.6 mm |
| $C_{14}$ | .509 | .536 | 168–179° C/0.9 mm |
| $C_{16}$ | .498 | .498 | 180–195° C/0.9 mm |
| $C_{17}$ | .419 | .432 | 52.6–56.9° C (M.P.) |
| $C_{18}$ | .500 | .500 | 57.6–59.1° C (M.P.) |
| $C_{20}$ | .357 | .367 | 64.0–64.9° C (M.P.) |

(b) 27.5 g, (0.100 moles) of n-tetradecylhydroxyethyl sulfide is dissolved in 1 liter of acetone in a 2 liter, single neck, round bottom flask. 11.9 g of 30.11% hydrogen peroxide, (0.105 moles) is added to this solution and the solution refluxed for 1½ hours. The solution is concentrated to 250 ml and cooled. The crystals are collected and washed twice with 25 ml of acetone and once with 60 ml acetone. The product is then air dried.

The data on the 2-(alkylsulfinyl)ethanols appear below:

TABLE II

| Alkyl Group | m.p. ° C |
|---|---|
| $C_{10}$ | 67.5–68.7 |
| $C_{12}$ | 72.5–73.3 |
| $C_{14}$ | 78.7–79.7 |
| $C_{16}$ | 84.3–85.4 |
| $C_{17}$ | 85.7–87.7 |
| $C_{18}$ | 88.8–90.2 |
| $C_{20}$ | 89.1–91.5 |

Melting points were determined with a Mettler hot stage microscope heated at 2°/minute.

(c) 15 g, 0.0515 moles of 2-(n-tetradecylsulfinyl)-ethanol are slurried with 75 ml dichloromethane. Then 2.15 ml (4.12 g, 0.0515 moles) of Sulfan, stabilized liquid sulfur trioxide, is dissolved in 50 ml of dichloromethane. The above solutions are mixed rapidly with stirring. The temperature increases to 35°. The reaction mixture results in a clear solution for several minutes; then, a solid separates. The reaction mixture is stirred for ½ hour and then poured into a 20% NaOH solution. The pH is adjusted to 8–9. The dichloromethane is removed by blowing dry nitrogen over the stirred embulsion at 40°. The aqueous solution is then freeze-dried. The dried solid is extracted with 600 ml hot 95% ethanol. The crystals which form on cooling are collected, washed with alcohol and vacuum dried at 35° over $P_2O_5$. Yield is 15.3 g, 75.7%. Analysis: by standard Hyamine titration. % Active = 100.3%. Similarly the other homologs were made. Purification of the sulfate product is by recrystallization from ethanol.

TABLE III

SODIUM 2-(n-ALKYLSULFINYL)ETHYL SULFATES

| Alkyl Group | % Active |
|---|---|
| $C_{10}$ | 99.7 |
| $C_{12}$ | 99.6 |
| $C_{14}$ | 100.3 |
| $C_{16}$ | 96.8 |
| $C_{18}$ | 95.5 |

Although the above reaction shows neutralization with NaOH, the preparation is not so limited. The potassium, ammonium, substituted ammonium and alkylol ammonium salts may also be prepared by using KOH, $NH_4OH$, or the appropriate amine.

The following examples will illustrate typical compositions utilizing the novel surfactants of the instant invention.

HARD SURFACE CLEANSER

| | % by weight |
|---|---|
| Sodium 2-(decylsulfinyl)ethyl sulfate | 2.0 |
| Sodium carbonate | 5.0 |
| Silica (200 mesh) | 93.0 |
| | 100.0 |

EXAMPLE 3

HARD SURFACE LIQUID CLEANER

| | % by weight |
|---|---|
| Sodium 2-(dodecylsulfinyl)ethyl sulfate | 2.0 |
| Tetrapotassium pyrophosphate | 15.0 |
| Lauric Diethanolamide | 4.0 |
| Water | 79.0 |
| | 100.0 |

EXAMPLE 4

LIGHT DUTY LIQUID DETERGENT COMPOSITION

| | % by weight |
|---|---|
| Ammonium 2-(tetradecylsulfinyl)ethyl sulfate | 15.0 |
| Ammonium lauryl alcohol - 3 mole ethylene oxide adduct sulfate | 15.0 |
| Lauric Diethanolamide | 6.0 |
| Perfume | 0.1 |
| Water | 63.9 |
| | 100.0 |

EXAMPLE 5

LIQUID HAIR SHAMPOO COMPOSITION

| | % by weight |
|---|---|
| Triethanolamine 2-(tetradecylsulfinyl)ethyl sulfate | 15.0 |
| Triethanolamine lauryl sulfate | 5.0 |
| Coco bis(hydroxyethyl)amine oxide | 5.0 |
| Ethanol | 6.0 |
| Perfume | 0.3 |
| Water | 68.7 |
| | 100.0 |

EXAMPLE 6

TOOTHPASTE COMPOSITION

| | % by weight |
|---|---|
| Sodium 2-(tetradecylsulfinyl)ethyl sulfate | 2.0 |
| Sorbitol | 14.0 |
| Glycerol | 11.0 |
| Calcium pyrophosphate | 42.0 |
| Flavoring Oils | 0.8 |
| Carboxymethyl cellulose | 0.2 |
| Water | 30.0 |
| | 100.0 |

EXAMPLE 7

ANTI-SCUMMING SOAP BAR

| | % by weight |
|---|---|
| Sodium 80:20 tallow coconut soap | 76.0 |
| Sodium 2-(hexadecylsulfinyl)ethyl sulfate | 10.0 |
| Perfume | 0.8 |
| Water | 13.2 |
| | 100.0 |

EXAMPLE 8

MECHANICAL DISHWASHING COMPOSITION

| | % by weight |
|---|---|
| Sodium 2-(octadecylsulfinyl)ethyl sulfate | 3.0 |
| Pluronic L-61 (supplier: BASF Wyandotte Corp.) | 1.5 |
| Sodium tripolyphosphate | 45.0 |
| Sodium silicate (2.4 $SiO_2/Na_2O$ ratio) | 12.0 |
| Potassium dichloroisocyanurate | 2.0 |
| Sodium sulfate | 36.4 |
| Perfume | 0.1 |
| | 100.0 |

EXAMPLE 9

HEAVY DUTY POWERED DETERGENT COMPOSITION

| | % by weight |
|---|---|
| Sodium 2-(alkylsulfinyl)ethyl sulfate wherein alkyl is a mixture of $C_{14}$, $C_{16}$ and $C_{18}$ chains in the ratio 1:2.5:2.5 | 18.0 |
| Coconut monoethanolamide | 3.0 |
| Sodium tripolyphosphate | 45.0 |
| Sodium silicate (2.4 $SiO_2/Na_2O$ ratio) | 8.0 |
| Sodium sulfate | 14.6 |
| Perfume and miscellaneous (optical whitener + colorants) | 0.2 |
| Carboxymethyl cellulose (D.S. = 0.7) | 0.4 |
| Water | 10.8 |
| | 100.0 |

EXAMPLE 10

NON-PHOSPHATE HEAVY DUTY POWDERED DETERGENT COMPOSITION

| | % by weight |
|---|---|
| Sodium 2-(hexadecylsulfinyl)ethyl sulfate | 9.0 |
| LAS (sodium $C_{10}$–$C_{15}$ linear alkyl benzene sulfonate | 11.0 |
| Lauric isopropanolamide | 3.0 |
| Sodium carbonate | 40.0 |
| Sodium silicate (2.4 $SiO_2/Na_2O$ ratio) | 15.0 |
| Sodium sulfate | 15.0 |
| Perfume and miscellaneous | 0.2 |
| Carboxymethyl cellulose | 0.5 |
| Water | 6.3 |
| | 100.0 |

EXAMPLE 11

NON-PHOSPHATE HEAVY DUTY LIQUID DETERGENT COMPOSITION

| | % by weight |
|---|---|
| Postassium 2-(hexadecylsulfinyl)ethyl sulfate | 10.0 |
| Lauryl dimethyl amine oxide | 5.0 |
| Potassium coconut soap | 2.0 |
| Trisodium citrate | 15.0 |
| Sodium silicate (2.5 $SiO_2/Na_2O$ ratio) | 10.0 |
| Carboxymethyl cellulose | 0.3 |
| Ethylene/maleic acid copolymer (sodium salt) | 0.5 |

-continued

| NON-PHOSPHATE HEAVY DUTY LIQUID DETERGENT COMPOSITION | % by weight |
|---|---|
| Perfume (including optical whitener and colorants) | 0.2 |
| Water | 57.0 |
| | 100.0 |

EXAMPLE 12

| UNBUILT NON-PHOSPHATE HEAVY DUTY LIQUID DETERGENT COMPOSITION | % by weight |
|---|---|
| Triethanolamine salt of 2-(alkylsulfinyl)ether sulfate wherein the alkyl group is a 1:2.5:2.5 mixture of n-$C_{14}$, $C_{16}$ and $C_{18}$ carbon chains | 10.0 |
| Neodol 45-7 ($C_{14}$–$C_{15}$ linear primary alcohol - 7 moles ethylene oxide adduct - Supplier: Shell Chemical Co.) | 30.0 |
| Sodium silicate (2.5 $SiO_2/Na_2O$ ratio) | 5.0 |
| Sodium coconut soap | 2.0 |
| Carboxymethyl cellulose | 0.3 |
| Perfume, colorants and optical whiteners | 0.2 |
| Water | 52.5 |
| | 100.0 |

EXAMPLE 13

| HEAVY DUTY POWDERED DETERGENT COMPOSITION WITH SOFTENING PROPERTIES | % by weight |
|---|---|
| Neodol 45-7 | 10.0 |
| Sodium 2-(alkylsulfinyl)ethyl sulfate wherein the alkyl group is a 1:1 mixture of n-$C_{18}$ and $C_{20}$ carbon chains) | 10.0 |
| Sodium tripolyphosphate | 40.0 |
| Sodium silicate (2.4 $SiO_2/Na_2O$ ratio) | 10.0 |
| Carboxymethyl cellulose | 0.4 |
| Perfume, colorants and whitening agents | 0.2 |
| Sodium sulfate | 19.4 |
| Water | 10.0 |
| | 100.0 |

As is apparent from the foregoing specific examples, the compositions provided by the invention may take the form of powders, liquids or bars (as well as pastes, flakes, beads or noodles) and may be formulated in heavy or light duty laundry detergents, hard surface and dishwashing compositions, floor cleaners, scouring cleansers, shampoos, dentifrices and mouthwash formulations.

EXAMPLES 14–20

In these Examples a typical laundry powder (minus the inert filler) is prepared and evaluated for detergency.

TABLE IV

| | % by weight |
|---|---|
| Na 2-(alkylsulfinyl)ethyl sulfate or other surfactant | 18 |
| Sodium tripolyphosphate | 50 |
| Sodium silicate (2.4 $SiO_2/Na_2O$ ratio) | 10 |
| Water | 22 |

The alkyl groups of the detergent active ranged from $C_{10}$ to $C_{18}$.

A washing solution is prepared by adding 1.5 g of the formulation of the instant invention to 1000 ml of 180 ppm water (2:1 $Ca^{++}/Mg^{++}$). The solution is heated to 120° F and placed in a Terg-O-Tometer with four 4 inches × 6½ inches standard soiled cloth swatches (65% Dacron/35% cotton soiled with vacuum cleaner dust). The initial pH of the solution is adjusted to 10. The container and contents are agitated for 10 minutes with the stirrer at 90 oscillations per minute. The cloth is removed, hand-squeezed and subsequently rinsed in fresh 180 ppm water for 1 minute, dried and examined with a Gardner Automatic Color Difference Meter, AC-3. The average reflectance of the washed cloths is compared with that obtained from the cloth washed either in solutions of corresponding formulations utilizing known standard surfactants or in solutions of partial formulations to show the dramatic increase in detergency when the novel compounds of the invention are also included in the formulation.

| Example No. | | Reflectance |
|---|---|---|
| 15 | Na 2-(decylsulfinyl)ethyl sulfate | 43.9 |
| 16 | Na 2-(dodecylsulfinyl)ethyl sulfate | 45.2 |
| 17 | Na 2-(tetradecylsulfinyl)ethyl sulfate | 53.8 |
| 18 | Na 2-(hexadecylsulfinyl)ethyl sulfate | 55.4 |
| 19 | Sodium lauryl sulfate | 45.7 |
| 20 | LAS (Sodium linear secondary alkyl ($C_{10}$–$C_{15}$) benzene sulfonate) | 57.2 |

EXAMPLES 21–26

Employing the same conditions of Examples 14–20 the standard soil cloths were washed at 80° F. The reflectances are shown in the Table below.

| Example No. | | Reflectance |
|---|---|---|
| 21 | Na 2-(decylsulfinyl)ethyl sulfate | 42.8 |
| 22 | Na 2-(dodecylsulfinyl)ethyl sulfate | 44.0 |
| 23 | Na 2-(tetradecylsulfinyl)ethyl sulfate | 52.5 |
| 24 | Na 2-(hexadecylsulfinyl)ethyl sulfate | 52.7 |
| 25 | Sodium lauryl sulfate | 45.1 |
| 26 | LAS | 57.8 |

EXAMPLES 27–30

The conditions of Example 14 were employed with the exception that the temperature was 140° F and only the $C_{14}$, $C_{16}$ and $C_{18}$ sulfinylethyl sulfates were used. The reflectometer values are shown below.

| Example No. | | Reflectance |
|---|---|---|
| 27 | Na 2-(tetradecylsulfinyl)ethyl sulfate | 55.2 |
| 28 | Na 2-(hexadecylsulfinyl)ethyl sulfate | 56.5 |
| 29 | Na 2-(octadecylsulfinyl)ethyl sulfate | 57.6 |
| 30 | LAS | 58.1 |

EXAMPLES 31–36

The procedure of Example 14 was followed with the only exeption being that the formulation was unbuilt and the active level was at 75%. The reflectometer values are shown below.

| Example No. | | Reflectance |
|---|---|---|
| 31 | Na 2-(decylsulfinyl)ethyl sulfate | 42.8 |
| 32 | Na 2-(dodecylsulfinyl)ethyl sulfate | 50.8 |
| 33 | Na 2-(tetradecylsulfinyl)ethyl sulfate | 55.8 |
| 34 | Na 2-(hexadecylsulfinyl)ethyl sulfate | 57.2 |

| Example No. | | Reflectance |
|---|---|---|
| 35 | LAS | 60.3 |
| 36 | Sodium lauryl sulfate | 53.0 |

EXAMPLES 37–40

The procedure of Example 14 was followed.

| Example No. | | Reflectance |
|---|---|---|
| 37 | Na 2-(tetradecylsulfinyl)ethyl sulfate | 53.6 |
| 38 | Na 2-(hexadecylsulfinyl)ethyl sulfate | 56.0 |
| 39 | Na 2-(octadecylsulfinyl)ethyl sulfate | 56.4 |
| 40 | LAS | 57.8 |

EXAMPLES 41–44

The procedure of Example 14 was followed.

| Example No. | | Reflectance |
|---|---|---|
| 41 | No surfactant-50% STPP-10% RU silicate solids | 43.4 |
| 42 | Na 2-(heptadecylsulfinyl)ethyl sulfate | 54.0 |
| 43 | Na 2-(hexadecylsulfinyl)ethyl sulfate | 55.0 |
| 44 | LAS | 56.5 |

EXAMPLES 45–48

The procedure of Example 14 is followed except that the formulation tested is as follows: 10% sodium 2-(alkylsulfinyl)ethyl sulfate, 40% builder as designated, 22% $Na_2SO_4$, 10% sodium silicate (2.4 $SiO_2/Na_2O$ ratio) and 10% water.

| Example No. | | Reflectance |
|---|---|---|
| 45 | Sodium 2-(hexadecylsulfinyl)ethyl sulfate + CMOS | 54.5 |
| 46 | Sodium 2-(hexadecylsulfinyl)ethyl sulfate + NTA | 56.3 |
| 47 | Sodium 2-(hexadecylsulfinyl)ethyl sulfate + trisodium citrate | 53.5 |
| 48 | Sodium 2-(hexadecylsulfinyl)ethyl sulfate + $Na_2CO_3$ | 56.7 |

CMOS = trisodium carboxymethyloxysuccinate, NTA = trisodium nitrilotriacetate.

These examples illustrate the use of the compounds of the invention with both organic and inorganic non-phosphate builders.

EXAMPLES 49–51

The following foaming tests are carried out in the presence of soil. Each of the three designated compounds, 0.051 millimole, is dissolved in 100 ml of 180 ppm (2:1 $Ca^{++}/Mg^{++}$) water and placed in a 250 ml stoppered graduated cylinder. 54 mg of a mixture of vacuum cleaner dust and synthetic sodium is added to each cylinder and the cylinders are then inverted 20 times and allowed to drain for 20 seconds. Foam volume readings are taken intially and at intervals over a 2 hour period.

| | | Volume of Foam (ml) | | | |
|---|---|---|---|---|---|
| Example | Compound | Initial | 30 min. | 60 min. | 120 min. |
| 49 | Neodol 45-7 | 40 | 26 | 14 | 6 |
| 50 | $n\text{-}C_{16}H_{33}\text{—}\overset{\overset{O}{\uparrow}}{S}\text{—}CH_2CH_2OSO_3Na$ | 36 | 18 | 12 | 10 |
| 51 | $n\text{-}C_{18}H_{37}\text{—}\overset{\overset{O}{\uparrow}}{S}\text{—}CH_2CH_2OSO_3Na$ | 20 | 4 | 2 | 0 |

Neodol 45-7 — trade name of the Shell Chemical Co. for a nonionic surfactant which is the seven mole ethoxylate of a blend of $C_{14}$ and $C_{15}$ linear primary alcohols.

EXAMPLES 52–54

The foaming tests in these examples are carried out in the same manner as for Examples 49–51 except that 0.034 millimole of each test compound is used.

| | | Volume of foam (ml) | | | |
|---|---|---|---|---|---|
| Example | Compound | Initial | 30 min. | 60 min. | 120 min. |
| 52 | Sterox SN | 46 | 14 | 8 | 0 |
| 53 | $n\text{-}C_{16}H_{33}\text{—}\overset{\overset{O}{\uparrow}}{S}\text{—}CH_2CH_2OSO_3Na$ | 20 | 12 | 8 | 4 |

-continued

| Example | Compound | Volume of foam (ml) | | | |
|---|---|---|---|---|---|
| | | Initial | 30 min. | 60 min. | 120 min. |
| 54 | n-C$_{18}$H$_{37}$—S(=O)—CH$_2$CH$_2$OSO$_3$Na | 12 | 4 | 2 | 0 |

Sterox SN — trade name of Monsanto Chemical Company for a nonionic surfactant which is the 13.5 mole ethoxylate of a blend of C$_{14}$ and C$_{15}$ linear primary alcohols.

EXAMPLES 55–57

The foaming tests in these examples are carried out in the same manner as for Examples 49–51 except that 0.0448 millimole of each test compounds is used.

| Example | Compound | Volume of foam (ml) | | | |
|---|---|---|---|---|---|
| | | Initial | 30 min. | 60 min. | 120 min. |
| 55 | Neodol 25-9 | 50 | 20 | 12 | 6 |
| 56 | n-C$_{16}$H$_{33}$—S(=O)—CH$_2$CH$_2$OSO$_3$Na | 28 | 18 | 16 | 10 |
| 57 | n-C$_{18}$H$_{37}$—S(=O)—CH$_2$CH$_2$OSO$_3$Na | 34 | 8 | 6 | 0 |

Neodol 25-9 — trade name of the Shell Chemical Company for a nonionic surfactant which is the 9 mole ethoxylate of a blend of C$_{12}$, C$_{13}$, C$_{14}$ and C$_{15}$ linear primary alcohols.

In the above Examples 49–57, the concentration of commercial nonionic corresponds to 0.27 g/liter which, in turn, corresponds to the level that would be present when a formulation containing 18% of the surfactant is utilized at a standard washing concentration of 1.5 g per liter. The compounds of the invention are tested on an equimolar basis for comparison purposes. The results show that the C$_{16}$ and C$_{18}$ alkyl compounds of the invention, and especially the C$_{18}$ alkyl compound, are lower foamers than the several standard nonionics in commercial use today.

What is claimed is:
1. A detergent composition comprising:
   a. a surfactant compound having the structure:

$$R-\overset{O}{\underset{\uparrow}{S}}-CH_2-CH_2-OSO_3M$$

wherein R is a straight chain saturated alkyl having from 10–20 carbon atoms and M is an alkali metal or ammonium cation; and
   b. a water-soluble organic or inorganic alkaline detergency builder salt, wherein the weight ratio of detergent active to builder salt is from 10:1 to about 1:10.
2. The detergent composition defined in claim 1 wherein the water-soluble inorganic alkaline builder salt is selected from the group consisting of alkali metal carbonates, borates, phosphates, polyphosphates, bicarbonates, silicates and hexametaphosphates; and the water-soluble organic alkaline builder salt is selected from the group consisting of aminopolycarboxylates, phytates, polyphosphonates, polycarboxylate homo- and copolymers, citrates, mellitates, carboxymethyloxysuccinates, oxydiacetates and mixtures thereof.
3. A detergent composition according to claim 1 wherein the surfactant is present from about 15% to about 25% and the builder is present from about 25% to about 50%.
4. A detergent composition according to claim 1 wherein the surface is sodium 2-(n-decylsulfinyl)ethyl sulfate.
5. A detergent composition according to claim 1 wherein the surfactant is sodium 2-(n-dodecylsulfinyl)ethyl sulfate.
6. A detergent composition according to claim 1 wherein the surfactant is sodium 2-(n-tetradecylsulfinyl)-ethyl sulfate.
7. A detergent composition according to claim 1 wherein the surfactant is sodium 2-(n-hexadecylsulfinyl)-ethyl sulfate.
8. A detergent composition according to claim 1 wherein the surfactant is sodium 2-(n-octadecylsulfinyl)-ethyl sulfate.
9. A detergent composition according to claim 1 wherein the surfactant is sodium 2-(n-eicosylsulfinyl)ethyl sulfate.
10. A detergent composition according to claim 1 wherein the surfactant is present from about 10% to about 75%.
11. A detergent composition comprising, as components, based on the total weight of said composition, about:
   a. from about 1% to about 75% of a surfactant compound having the structure:

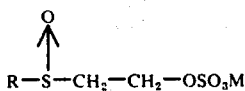

wherein R is a straight chain saturated alkyl having from 10–20 carbon atoms and M is an alkali metal or ammonium cation,
b. 1% to about 60% of another detergent compound selected from the group consisting of anionic, nonionic, zwitterionic or ampholytic detergent compounds and mixtures thereof,
c. 0% to about 50% of a water-soluble organic or inorganic alkaline detergency builder salt.

12. The detergent composition defined in claim 11 wherein the water-soluble inorganic alkaline builder salt is selected from the group consisting of alkali metal carbonates, borates, phosphates, polyphosphates, bicarbonates, silicates and hexametaphosphates; and the water-soluble organic alkaline builder salt is selected from the group consisting of aminopolycarboxylates, phytates, polyphosphonates, polycarboxylate homo- and copolymers, citrates, mellitates, carboxymethyloxysuccinates, oxydiacetates and mixtures thereof.

13. The composition of claim 11 wherein the surfactant compound is present from about 10% to about 75%.

14. The composition of claim 11 wherein the surfactant is sodium 2-(n-decylsulfinyl)ethyl sulfate.

15. The composition of claim 11 wherein the surfactant is sodium 2-(n-dodecylsulfinyl)ethyl sulfate.

16. The composition of claim 11 wherein the surfactant is sodium 2-(n-tetradecylsulfinyl)ethyl sulfate.

17. The composition of claim 11 wherein the surfactant is sodium 2-(n-hexadecylsulfinyl)ethyl sulfate.

18. The composition of claim 11 wherein the surfactant is sodium 2-(n-octadecylsulfinyl)ethyl sulfate.

19. The composition of claim 11 wherein the surfactant is sodium 2-(n-eicosylsulfinyl)ethyl sulfate.

* * * * *

UNITED STATES PATENT AND TRADEMARK OFFICE
CERTIFICATE OF CORRECTION

PATENT NO. : 3,986,986
DATED : October 19, 1976
INVENTOR(S) : Vincent Lamberti and Wilder F. Pease It is certified that error appears in the above-identified patent and that said Letters Patent are hereby corrected as shown below:

Column 6, line 47 - "Netherlands Pat. No." should be -- Netherlands Specification No. --.

Column 9, line 4 - Add -- EXAMPLE 2 --.

Column 11, line 16 - "2-(alkylsulfinyl)ether" should be -- 2-(alkylsulfinyl)ethyl --.

Column 14, line 24 - "sodium" should be -- sebum --.

Column 16, line 44 - "surface" should be -- surfactant --

Column 16, lines 47,48 - "2-(n-dodecylsulfinyl-)ethyl" should be -- 2-(n-dodecylsulfinyl)ethyl --;

Column 16, line 51 - "2-(n-tetradecylsulfinyl)-ethyl" should be -- 2-(n-hexadecylsulfinyl)ethyl --;

Column 16, line 54 - "2-(n-hexadecylsulfinyl)-ethyl" should be -- 2-(n-hexadecylsulfinyl)ethyl --;

Column 16, line 57 - "2-(n-octadecylsulfinyl)-ethyl" should be -- 2-(n-octadecylsulfinyl)ethyl --;

Column 16, lines 59,60 - "2-(n-eicosylsulfinyl-)ethyl" should be -- 2-(n-eicosylsulfinyl)ethyl --.

Signed and Sealed this

Eleventh Day of January 1977

[SEAL]

Attest:

RUTH C. MASON
*Attesting Officer*

C. MARSHALL DANN
*Commissioner of Patents and Trademarks*